United States Patent [19]

Walgenbach

[11] Patent Number: 4,695,564

[45] Date of Patent: Sep. 22, 1987

[54] INSECTICIDAL COMPOSITIONS COMPRISING A SYNERGISTIC MIXTURE OF TERBUFOS OR PHORATE AND A PYRETHROID

[75] Inventor: Paul J. Walgenbach, Hamilton, N.J.

[73] Assignee: American Cyanamid Company, Stamford, Conn.

[21] Appl. No.: 831,605

[22] Filed: Feb. 25, 1986

Related U.S. Application Data

[63] Continuation-in-part of Ser. No. 709,617, Mar. 8, 1985, abandoned.

[51] Int. Cl.[4] ...................... A01N 37/34; A01N 57/00
[52] U.S. Cl. ...................................... 514/127; 514/521
[58] Field of Search ................................ 514/127, 521

[56] References Cited

U.S. PATENT DOCUMENTS

| 2,596,076 | 5/1952 | Hook et al. ........................ | 514/127 |
| 2,759,010 | 8/1956 | Lorenz et al. ..................... | 514/127 |
| 4,065,558 | 12/1977 | Gordon ............................. | 514/127 |
| 4,199,595 | 4/1980 | Berkelhammer et al. .......... | 514/521 |
| 4,362,722 | 12/1982 | Stubb ................................ | 514/127 |

Primary Examiner—Allen J. Robinson
Attorney, Agent, or Firm—Alice C. Brennan

[57] ABSTRACT

The present invention relates to insecticidal compositions comprising a mixture of a pyrethroid and 0,0-diethyl S-[(ethylthio)methyl]phosphorodithioate or S-[[(1,1-dimethylethyl)thio]methyl] 0,0-diethylphosphorodithioate. The invention also relates to a method of controlling insect pests and additionally providing protection from cutworms (Lepidoptera:Noctuidae) of an agronomic crop utilizing granular compositions of the invention.

7 Claims, No Drawings

INSECTICIDAL COMPOSITIONS COMPRISING A SYNERGISTIC MIXTURE OF TERBUFOS OR PHORATE AND A PYRETHROID

This application is a continuation-in-part of application Ser. No. 709,617, filed on Mar. 8, 1985, now abandoned.

BACKGROUND OF THE INVENTION

Noctuid larvae, named commonly as cutworms, armyworms, loopers, semiloopers, leafworms, borers, and fruitworms represent a serious problem in crops such as corn, cotton, tobacco, rice and many vegetables. Infestation and resulting damage to crops due to these pests vary greatly from year to year depending upon climatic conditions and weather patterns. As such, treatments such as sprays and baits are normally only applied after a dangerous infestation has been identified. Rescue treatments of this type are usually effective. However, in order for this type of treatment to be effective for preventing destruction of seedling stands, an infestation must be discovered early and treated promptly. Black cutworms in particular can be highly destructive to corn, due to their habit of eating the stem of a plant, cutting it down at ground level. Damage from this pest can make it necessary to replant large quantities of corn if not treated promptly and effectively.

One insecticidal composition which is commonly used for the control of pests, such as mites, which attack corn, cotton, and many vegetables is phorate (O,O-diethyl S-[(ethylthio)methyl]phosphorodithioate). This insecticide is normally applied in granular formulations as a band concurrently with the planting operation. (See U.S. Pat. Nos. 2,596,076 and 2,759,010).

Another insecticidal composition which is used for the control of pests, such as maize billbugs, Southern corn billbugs, cutworms, lesser cornstalk borers, symphylans and nematodes, which attack corn, sugar beets and grain sorghum is terbufos (S-[[1,1-dimethylethyl]-thio]methy) O,O-diethylphosphorodithioate). This insecticide is normally applied in granular formulation as a band at planting. (See, U.S. Pat. Nos. 2,596,076 and 4,065,558)

U.S. Pat. No. 4,199,595 discloses synthetic pyrethroid flucythrinate, (±)-cyano-(3-phenoxyphenyl) methyl (+)-4-(difluoromethoxy)-alpha-(1-methylethyl) benzeneacetate and its preparation. This insecticide is used for the control of pests, such as cutworms, corn earworms, fall armyworms, European corn borers and aphids.

SUMMARY OF THE INVENTION

The invention relates to insecticidal compositions comprising a mixture of a pyrethroid with O,O-diethyl S-[(ethylthio)methyl]phosphorodithioate (phorate), or S[[(1,1-dimethylethyl)thio]methyl] O,O-diethylphosphorodithioate (terbufos), and methods of controlling insect pests and/or providing protection from black cutworm infestation and damage.

Typical pyrethroids are (±)-α-cyano-m-phenoxybenzyl (±)-2-[p-(difluoromethoxy) phenyl]-3-methylbutyrate (flucythrinate), cyano-(3-phenoxyphenyl)-methyl-4-chloro-α-(1-methylethyl) benzeneacetate (fenvalerate) and cypermethrin.

In accordance with the invention, a single application of the insecticidal compositions, at planting time provides effective control of a wide variety of pests and additionally affords protection against black cutworm. This avoids the disadvantages of the prior art treatment since there is no need for rescue follow-up. Thus, the present composition avoids the expense connected with rescue treatments. Additionally, it has been found that the present compositions also provide control of Lepidoptera in excess of the expected control attributable to each of the insecticidal components.

DESCRIPTION OF THE PREFERRED EMBODIMENTS

In accordance with the invention, the compositions provided effective control of a wide variety of insect pests, such as cutworms, corn rootworms, wireworms, white grubs, seedcorn maggots, seedcorn beetles, flea beetles, European corn borers, corn leaf aphids and spider mites. It may be applied as granular compositions containing 1% to 25% by weight of phorate or terbufos and a minimum of 0.1% to 2.5% by weight of pyrethroid on sorptive or non-sorptive particulate granular particles such as diatomites, clays such as kaoline, attapulgite, montmorillonite, limestone, ground corn cobs, sand silica activated carbon and the like.

When non-sorptive carriers are used, the surface of the particles may be wetted with the active materials and then coated with finely ground clay, talc, walnut shell flour, or other inert material. A binder or sticking agent may also be added to assure the adherence of the active material to the particles.

In the case of sorptive carriers such as clays, the clay particles are treated with a polyol deactivator such as an alkylene glycol, diethylene glycol, propylene glycol, triethylene glycol, polyethylene glycol, and the like. About 1% to 20% by weight of the deactivator is used to avoid stability problems.

The results obtained by varying the ratios of the components of the instant compositions are shown in Table I. It can be seen that compositions containing 10/1 to 40/1 weight ratios of phorate or terbufos to flucythrinate are useful. For application under growing conditions normal application rates as a broadcast application for phorate and terbufos are in the 1.0 to 3.0 lb/acre range and preferred compositions of the invention would provide a minimum of from 0.01 to 0.09 lbs/acre of flucythrinate on a broadcast basis. However, it should be recognized that under varying insect pressure and climatic conditions actual rates of application may vary while maintaining 10/1 to 40/1 weight ratio of the components.

TABLE I

Topical $LD_{50}$ in ng/worm
(Southern Armyworms, Third Instar)

| | Treatment | $LD_{50}$ (ng/worm) | $LD_{50}$ (ng/worm) |
|---|---|---|---|
| a | Treatment | $LD_{50}$ (ng/worm) | $LD_{50}$ (ng/worm) |
| a | Phorate | 747.0* | 747.0* |
| b | Flucythrinate | 11.53* | 11.53* |
| a/b | 10/1 | 9.8+ | 95 + 9.5 |
| a/b | 20/1 | 4.8+ | -95 + 4.7 |
| a/b | 30/1 | 7.1+ | 202 + 6.7 |
| a/b | 40/1 | 4.9+ | 189 + 4.7 |
| c | Terbufos | 204.0* | 204.0* |
| b | Flucythrinate | 11.53* | 11.53* |
| c/b | 10/1 | 3.8+ | 37 + 3.7 |
| c/b | 20/1 | 2.9+ | 55 + 2.8 |
| c/b | 30/1 | 4.6+ | 129 + 4.3 |

TABLE I-continued

Topical LD$_{50}$ in ng/worm
(Southern Armyworms, Third Instar)

| c/b | 40/1 | 3.6+ | 136 + 3.4 |
|---|---|---|---|

*Average value of all tests.
+IN FLUCYTHRINATE EQUIVALENTS
Flucythrinate equivalents = (Potency Ratio) (Weight of Organo Phosphate) + Weight of Flucythrinate
where potency ratio = $\frac{LD_{50} \text{ flucythrinate}}{LD_{50} \text{ organosphosphate}}$ For convenience, rates of application are expressed on a broadcast basis, which represents the total amounts of material which would be present if the compositions were evenly distributed over a one acre plot. In practice, granular compositions of this type are frequently applied as "banded" treatments over the rows of planted crops and are frequently expressed in terms of ounces per 1,000 feet of row. Thus, this type of application can result in varying expressions of concentration of materials in localized areas depending upon the spacing of the crops. Expression of application rates on a broadcast basis readily enables conversion to other application practices.

In order to demonstrate the present invention, the following examples are given primarily as an illustration. No specific details or enumerations contained therein should be construed as limitations on the present invention except insofas as they appear in the appended claims. All parts and percentages are by weight unless otherwise specifically designated.

EXAMPLE 1

Preparation of granular compositions

The general procedures for the preparation of granular pesticidal compositions of the invention.

Method A

The desired quantity of granules is charged into a suitable pill coater apparatus modified by the addition of aluminum blades to facilitate the mixing and the flow of clay particles through the spray stream. The required amount of each toxicant (and deactivator, if desired) is placed in a stainless steel sprayer adapted so that a nozzle, screen and tip can be used. The container is pressurized to 1.75 kg/cm$^2$. The pill coater is started and the toxicant spray stream directed down and into the flowing granules. The sprayer is shaken at intervals to insure a homogeneous spray solution. After the contents have been sprayed, the container is rinsed with a small amount of methylene chloride and spray rinsed onto the granules, and the granules dried by evaporating the methylene chloride.

Method B

The desired quantity of granules is charged into a hexagonal polyethylene bowl attached to a variable speed laboratory mixer. The speed of the mixer is adjusted so that the granules cascade down the side of the bowl. The toxicant(s) and deactivator are placed in a 40 mL capacity DeVilbis bottle. A DeVilbis nozzle is attached to the bottle, the air pressure is adjusted to 0.14 to 0.21 kg/cm$^2$ and the contents sprayed onto the cascading granules. After the contents have been sprayed, the container is rinsed with a small amount of methylene chloride and spray rinsed onto the granules, and the granules dried by evaporating the methylene chloride.

Utilizing the above procedures and varying the amounts and ratios of flucythrinate and phorate or flucythrinate and terbufos yields the granular compositions listed in Table II below.

TABLE II

| Granular compositions % toxicant by weight | | |
|---|---|---|
| Composition Number | % Flucychrinate | % Phorate |
| 1 | 0.1 | 10 |
| 2 | 0.33 | 10 |
| 3 | 0.50 | 10 |
| 4 | 0.67 | 10 |
| 5 | 1.0 | 10 |
| 6 | 0.1 | 15 |
| 7 | 0.38 | 15 |
| 8 | 0.56 | 15 |
| 9 | 0.67 | 15 |
| 10 | 0.75 | 15 |
| 11 | 1.0 | 15 |
| | % Flycythrinate | % Terbufos |
| 12 | 0.1 | 10 |
| 13 | 0.33 | 10 |
| 14 | 0.50 | 10 |
| 15 | 0.67 | 10 |
| 16 | 1.0 | 10 |
| 17 | 0.1 | 15 |
| 18 | 0.38 | 15 |
| 19 | 0.56 | 15 |
| 20 | 0.67 | 15 |
| 21 | 0.75 | 15 |
| 22 | 1.0 | 15 |

EXAMPLE 2

Effectiveness of various ratios against southern armyworms

The toxicity of various ratios of flucythrinate/phorate and flucythrinate/terbufos compositions to third instar southern armyworms (*Spodoptera eridania*) is determined by topical application of microdrops of the mixtures in acetone solution to the dorsum of the insect. The results of these experiments which are summarized in Table III below demonstrate the improvement in insecticidal activity expressed as LD50 values, obtained with composition of the invention when compared to each of the components individually.

TABLE III

| Toxicity of compositions against third instar southern armyworms | | | |
|---|---|---|---|
| Ratio | Component | Topical $LD_{50}$, ng/worm | Topical $LD_{50}$ Expressed As Flucythrinate Equivalents ng/worm |
| — | a. Phorate | 651.0 | 9.8 |
| — | b. Flucythrinate | 18.5 | |
| 10:1 | a:b | 95 + 9.5 | |
| 20:1 | a | 927.0 | 4.8 |
| | b | 12.5 | |
| | a:b | 95 + 4.7 | |
| 30:1 | a | 718.0 | 7.1 |
| | b | 11.3 | |
| | a:b | 202 + 6.7 | |
| 40:1 | a | 695.0 | 4.9 |
| | b | 9.4 | |
| | a:b | 189 + 4.7 | |
| 10:1 | c. Terbufos | 251.0 | 3.8 |
| | b | .6.9 | |
| | c:b | 37 + 3.7 | |
| 20:1 | c | 183.0 | 2.9 |
| | b | 9.1 | |
| | c:b | 55 + 2.8 | |
| 30:1 | c | 232.0 | 4.6 |

TABLE III-continued Toxicity of compositions against third instar southern armyworms

| Ratio | Component | Topical LD$_{50}$, ng/worm | Topical LD$_{50}$ Expressed As Flucythrinate Equivalents ng/worm |
|---|---|---|---|
| | b | 15.7 | |
| | c:b | 129 + 4.3 | |
| 40:1 | c | 150.0 | 3.6 |
| | b | 8.8 | |
| | c:b | 136 + 3.4 | |

EXAMPLE 3

Effectiveness of compositions of the invention against black cutworms (*Agrotis ipsilon*)

Granular treatments are applied with planter mounted applicators and seven inch banders behind the planter shoes and in front of a press wheel. Treatments are applied at planting to a plot consisting of a single row of corn ten feet long, surrounded by an aluminum lawn edging as a barrier. When the seedlings have reached the two-leaf stage, black cutworms which have been grown in a rearing room to the fourth instar, the stage at which they begin cutting plants, are released in each plot over a two week period as shown in Table IV below to simulate a natural infestation of the pest in its destructive stages. Three weeks after the onset of infestation the plots are evaluated and the damage attributed to the black cutworms recorded. The results of these experiments utilizing some of the compositions identified in Example 1 are summarized in Table V below and demonstrate the effectiveness of compositions of the invention in providing protection to seedling corn from black cutworms.

TABLE IV

Artificial infestation of black cutworm larvae into plots

| Day of release | Number of larvae released per plot | Instar of larvae |
|---|---|---|
| 1 | 5 | 4–5 |
| 3 | 6 | 4–5 |
| 4 | 5 | 4–5 |
| 10 | 3 | 4–5 |
| 11 | 4 | 4–5 |

TABLE V

Effectiveness of compositions of the invention in providing protection of seedling corn

| Composition number | OZ 1000' | lbs ac/A (broadcast) | lbs ac/A (treated zone) | % control compared untreated control |
|---|---|---|---|---|
| Control | 0 | 0 | 0 | 0 |
| 2 | 9 | 1.0/0.033 | 4.3/0.04 | 12 |
| 4 | 9 | 1.0/0.067 | 4.3/0.14 | 50 |
| 7 | 8 | 1.3/0.033 | 5.6/0.14 | 100 |
| 8 | 8 | 1.3/0.049 | 5.6/0.21 | 47 |
| 10 | 8 | 1.3/0.065 | 5.6/0.28 | 60 |
| 13 | 9 | 1.0/0.010 | 4.3/0.04 | 38 |
| 15 | 9 | 1.0/0.003 | 4.3/0.14 | 41 |
| 19 | 8 | 1.3/0.044 | 5.6/0.19 | 28 |
| 22 | 9 | 1.0/0.067 | 4.3/0.29 | 62 |

EXAMPLE IV

Effectiveness of various ratios against southern armyworms

The toxicity of various ratios of fenvalerate/phorate, fenvalerate/terbufos, cypermethrin/phorate and cypermethrin/terbufos compositions to third instar southern armyworms (*Spodoptera eridania*) is determined by topical application microdrops of the mixtures in active solution to the dorsum of the larval thoracic segment. After treatment of each tray of dishes a Siava lime bean leaf was placed on each dish as a food source. The results of these experiments which are summarized in Table VI below demonstrate the insecticidal activity, expressed as LD$_{50}$ values, obtained with composition of the invention when compared to each of the components individually.

TABLE VI

Toxicity of compositions against third instar southern armyworms

| Ratio | Component | Topical LD$_{50}$ micrograms solution/ Grams larval Wt | Topical LD$_{50}$ Expressed As Pyrethroid micrograms solution/ Grams Larval Wt |
|---|---|---|---|
| | a. Phorate | 126.78 | |
| | d. Cypermethrin | 1.76 | |
| 10:1 | a:d | | 3.37 |
| 20:1 | a:d | | 3.44 |
| 30:1 | a:d | | 1.78 |
| 40:1 | a:d | | 2.46 |
| | c. Terbufos | 33.26 | |
| | d. Cypermethrin | 3.94 | |
| 10:1 | c:d | | 1.80 |
| 20:1 | c:d | | 1.22 |
| 30:1 | c:d | | 0.73 |
| 40:1 | c:d | | 0.78 |
| | a. Phorate | 120.66 | |
| | e. Fenvalerate | 0.99 | |
| 10:1 | a:e | | 1.62 |
| 20:1 | a:e | | 1.19 |
| 30:1 | a:e | | 1.13 |
| 40:1 | a:e | | 0.89 |
| | c. Terbufos | 68.84 | |
| | e. Fenvalerate | 1.85 | |
| 10:1 | c:e | | 1.35 |
| 20:1 | c:e | | 1.03 |
| 30:1 | c:e | | 1.87 |
| 40:1 | c:e | | 0.58 |

What is claimed is:

1. An insecticidal composition comprising a synergistic mixture of 10 to 40 parts by weight of 0,0-diethyl S-[(ethylthio)methyl]phosphorodithioate or S[[(1,1-dimethylethyl)thio]methyl] 0,0-diethylphosphorodithioate and 1 part by weight of a pyrethroid selected from the group consisting of (±)-α-cyano-m-phenoxybenzyl (±)-2-[p-(difluoromethoxy) phenyl]-3-methylbutyrate, cyano-(3-phenoxyphenyl)-methyl-4-chloro-α-(1-methylethyl) benzeneacetate and (±)-α-cyano-3-phenoxbenzyl-(±)-cis, trans-3-(2,2-dichlorovinyl)-2,2-dimethylcylopropane carboxylate.

2. An insecticidal composition according to claim 1, wherein the pyrethroid is (±)-α-cyano-m-phenoxybenzyl (±)-2-[p-(difluoromethoxy) phenyl]-3-methylbutyrate.

3. An insecticidal compositon according to claims 1 or 2 which further comprises about 75% to 95% by weight of a sorptive or non-sorptive particulate granular particle.

4. An insecticidal composition comprising a synergistic mixture of 10 to 40 parts by weight of S-[[1,1-dimethylethyl)thio]methyl] 0,0-diethylphosphorodithioate and 1 part by weight of cyano-(3-phenoxyphenyl)-methyl-4-chloro-alpha-(1-methylethyl) benzeneacetate.

5. An insecticidal composition according to claim 4 which further comprises about 75% to 95% by weight of a sorptive or non-sorptive particulate granular particle.

6. A method for controlling insect pests and providing protection from black cutworms (Lepidotera:Noctuidae) comprising applying to the soil or in the furrow an insecticidally effective amount of the composition of claim 4.

7. A method for controlling insect pests and providing protection from black cutowrms (Lepidotera:Noctuidae) comprising applying to the soil or in the furrow an insecticidally effective amount of the composition of claim 1.

* * * * *